US00PP19702P2

(12) United States Plant Patent
Unger

(10) Patent No.: US PP19,702 P2
(45) Date of Patent: Feb. 10, 2009

(54) ***SALVIA* PLANT NAMES 'SAL CERV 07'**

(50) Latin Name: *Salvia hybrida*
Varietal Denomination: Sal Cerv 07

(76) Inventor: Christiaan Unger, Robert Koch Strasse 7, Worms (DE), 67511

( * ) Notice: Subject to any disclaimer, the term of this patent is extended or adjusted under 35 U.S.C. 154(b) by 25 days.

(21) Appl. No.: 11/824,145

(22) Filed: Jun. 30, 2007

(51) Int. Cl.
*A01H 5/00* (2006.01)

(52) U.S. Cl. ..... Plt./475
(58) Field of Classification Search ..... Plt./475
See application file for complete search history.

*Primary Examiner*—Kent L Bell

(57) ABSTRACT

A new and distinct *Salvia* plant cultivar is disclosed, characterized by an upright, very compact growth habit; dark green foliage; bright red flowers and a long inflorescence longevity.

1 Drawing Sheet

Latin name of the genus and species: *Salvia hybrida.*
Variety denomination: 'Sal Cerv 07'.

BACKGROUND OF THE INVENTION

The new cultivar is a product of open pollination of *Salvia stephavophylla* in September 2003. It was discovered and selected by Christiaan Unger in October 2004 in Rheinfelden, Germany.

Asexual reproduction of the new cultivar 'SAL CERV 07' by vegetative cuttings was performed in Oxnard, Calif., and has shown that the unique features of this cultivar are stable and reproduced true to type on successive generations.

SUMMARY OF THE INVENTION

The cultivar 'SAL CERV 07' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAL CERV 07.' These characteristics in combination distinguish 'Sal Cerv 07' as a new and distinct *Salvia* cultivar:

1. Upright, slightly mounding, compact growth habit;
2. Dark green foliage;
3. Bright red flowers; and
4. A long inflorescence longevity.

Plants of the new cultivar differ from plants of the unnamed female parent selection in growth habit and size and level of heat tolerance.

In comparison to the commercially available variety 'Rhapsody in Blue' (U.S. Plant Pat. No. 15,148), 'SAL CERV 07' is shorter and has a smaller plant spread. Additionally, the new variety 'SAL CERV 07' has darker green foliage. Also, there are less inflorescences per spike on 'SAL CERV 07' and the flocculent texture is more prolific on the upper lip of 'SAL CERV 07' than the comparable variety. Finally, the new variety 'Sal Cerv 07' has red inflorescences compared to the violet-blue of 'Rhapsody in Blue' and the new cultivar has a longer inflorescence longevity.

BRIEF DESCRIPTION OF THE PHOTOGRAPH

The accompanying photograph in FIG. 1 illustrates in full color a typical plant of 'SAL CERV 07' grown in a six inch container in a greenhouse. One cutting was used in the pot. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'Sal Cerv 07' plants grown in Oxnard, Calif. during the months of January through June in an outdoor garden. The growing temperature ranged from 12° C. to 15° C. at night to 12° C. to 20° C. during the day. Measurements and numerical values represent averages of typical flowering types.

Botanical classification: *Salvia hybrida* cultivar 'Sal Cerv 07.'
Commercial classification: Hybrid Sage.

PROPAGATION

Time to rooting: 10 to 13 days at 20° C.
Root description: Moderately thick.

PLANT

Growth habit: Upright, slightly mounding compact herbaceous perennial.
Height: Approximately 35 cm.
Plant spread: Approximately 30 cm.
Growth rate: Moderate.
Branching characteristics: Freely branching.
Length of lateral branches: Approximately 28 cm.
Number of leaves per lateral branch: Approximately 16.
Internode length: Approximately 3.2 cm.
Age of plant described: Approximately 139 days.

FOLIAGE

Leaf:
*Arrangement.*—Opposite.
*Average length.*—Approximately 2.9 cm.
*Average width.*—Approximately 1.8 cm.
*Shape of blade.*—Ovate.
*Apex.*—Broadly acuminate.
*Base.*—Rounded.
*Attachment.*—Petiolate.
*Margin.*—Crenate.
*Texture of top surface.*—Lightly pubescent.
*Texture of bottom surface.*—Lightly pubescent.
*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.
*Venation.*—Type: Pinnate. Venation color upper side: Near Yellow-Green 147C. Venation color under side: Near Yellow-Green 147C.

Petiole:
*Average length.*—Approximately 1.4 cm.
*Color.*—Near Yellow-Green 147C.
*Diameter.*—Approximately 0.1 cm.

INFLORESCENCE DESCRIPTION

Natural flowering season: Blooms almost continuously from January into July.
Inflorescence type: Raceme.
Aspect: Outward.
Flower number per lateral branch: Between 3 and 14.
Inflorescence shape: Winged.
Total inflorescence size:
*Diameter.*—Approximately 0.6 cm.
*Length.*—Approximately 2 cm.
Inflorescence longevity: Individual flowers last about 6 to 8 days.
Persistence: Not persistent.
Inflorescence fragrance: None.
Inflorescence bud:
*Length.*—Approximately 0.4 cm.
*Diameter.*—Approximately 0.3 cm.
*Form.*—Globular.
*Color.*—Near Red 46A.

Petals:
*Arrangement.*—Labiate.
*Length.*—Upper Petal: Approximately 1.7 cm. Lower Petal: Approximately 1 cm.
*Width.*—Upper Petal: Approximately 0.3 cm. Lower Petal: Approximately 0.5 cm.
*Shape.*—Upper Petal: Broadly elliptic. Lower Petal: Spatulate.
*Apex.*—Upper Petal: Emarginate. Lower Petal: Emarginate.
*Base.*—Fused.
*Petal texture.*—Flocculent for upper petal and lightly pubescent on lower petals.
*Petal margin.*—Entire for both upper and lower petals.
*Petal color.*—First opening: Near Red 46A. Maturity: Near Red 44A. Fading: Near Red 46B.

Sepals:
*Arrangement.*—Three sepals fused into a tube.
*Length.*—Approximately 1.4 cm.
*Width.*—Approximately 0.6 cm.
*Shape.*—Elliptic.
*Apex.*—Acuminate.
*Margin.*—Entire.
*Texture.*—Lightly pubescent.
*Color.*—First opening upper surface: Near Brown 200A. First opening lower surface: Near Green 143A. Fully opened upper surface: Near Brown 200A. Fully opened lower surface: Near Green 143A.

Peduncle:
*Length.*—Approximately 1.2 cm.
*Diameter.*—Approximate 0.1 cm.
*Strength.*—Moderate.
*Color.*—Near Green 143A.

REPRODUCTIVE ORGANS

Stamens:
*Quantity per flower.*—Two.
*Anther shape.*—Narrowly elliptic.
*Anther length.*—About 1.8 mm.
*Anther color.*—Near Greyed-Orange 177B.
*Filament length.*—About 1 cm.
*Filament color.*—Near Red 42A.
*Pollen amount.*—None observed.

Pistils:
*Quantity per flower.*—One.
*Pistil length.*—About 2 cm.
*Stigma shape.*—Two-parted, cleft.
*Stigma color.*—Near Red 42B.
*Style length.*—About 1.9 cm.
*Style color.*—Near Red 38D.
*Ovary color.*—Near Green 143D.

OTHER CHARACTERISTICS

Disease resistance: Neither resistance nor susceptibility to diseases or pests has been observed in this variety.
Drought tolerance/cold tolerance: The new cultivar can tolerate temperatures from −25 to 35° C. The new cultivar has a winter dormancy where there are no flowers on the plant.
Fruit/seed production: Not observed because commercially the plants are discarded or the flowers removed before seed set occurs.

What is claimed is:

1. A new and distinct cultivar of *Salvia* plant named 'SAL CERV 07' as herein illustrated and described.

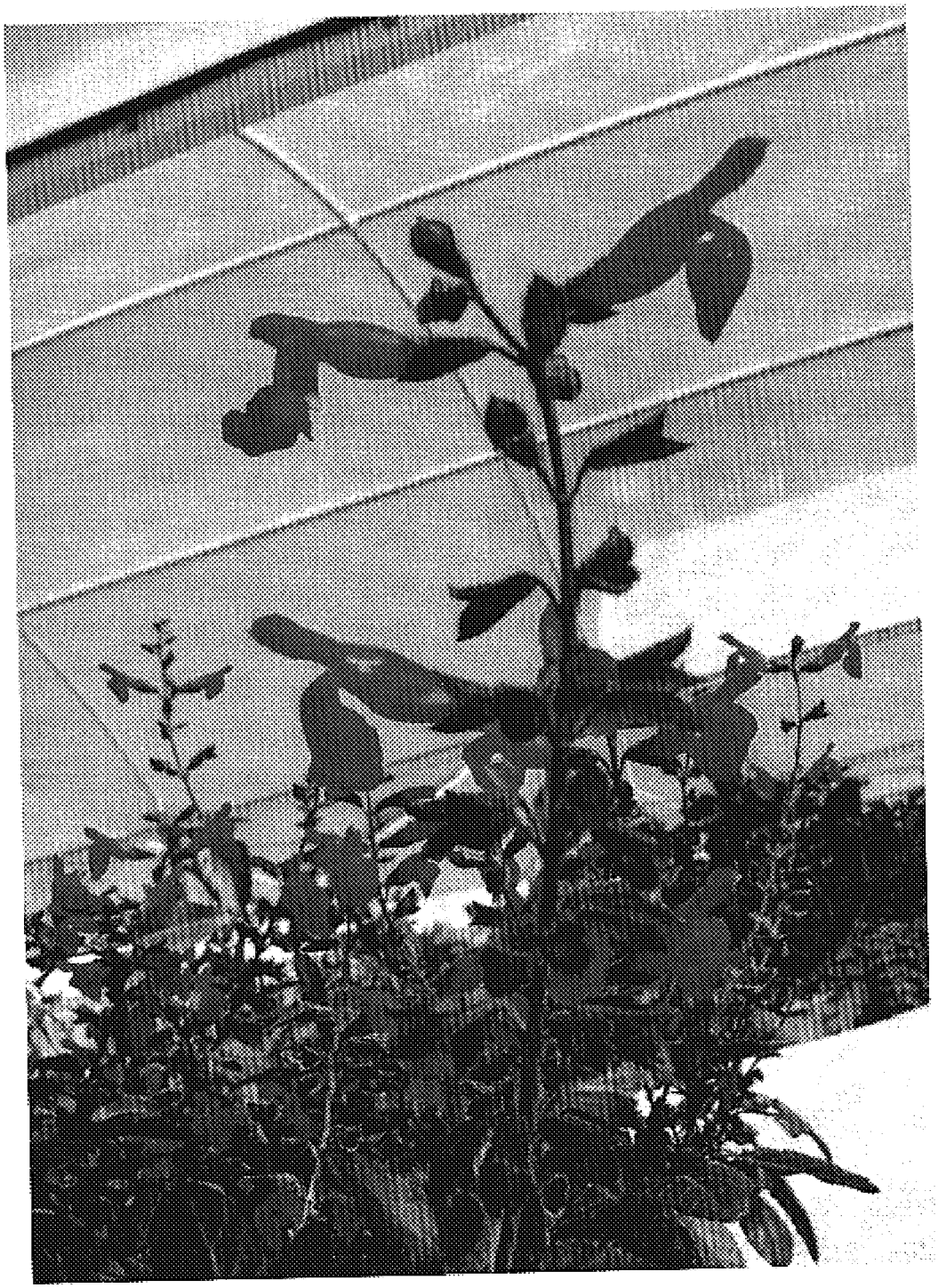

* * * * *